(12) United States Patent
Borst et al.

(10) Patent No.: US 10,266,697 B2
(45) Date of Patent: Apr. 23, 2019

(54) YELLOW METHINE DYES

(71) Applicant: LANXESS Deutschland GmbH, Cologne (DE)

(72) Inventors: Hans-Ulrich Borst, Elsdorf (DE); Frank Linke, Cologne (DE); Stephan Michaelis, Odenthal (DE)

(73) Assignee: LANXESS Deutschland GmbH, Cologne (DE)

(\*) Notice: Subject to any disclaimer, the term of this patent is extended or adjusted under 35 U.S.C. 154(b) by 10 days.

(21) Appl. No.: 15/535,766

(22) PCT Filed: Dec. 22, 2015

(86) PCT No.: PCT/EP2015/080973
§ 371 (c)(1),
(2) Date: Jun. 14, 2017

(87) PCT Pub. No.: WO2016/116244
PCT Pub. Date: Jul. 28, 2016

(65) Prior Publication Data
US 2017/0349752 A1 Dec. 7, 2017

(30) Foreign Application Priority Data
Jan. 21, 2015 (EP) .................................... 15151917

(51) Int. Cl.
| | |
|---|---|
| *C08J 3/12* | (2006.01) |
| *C08J 3/20* | (2006.01) |
| *C08K 5/00* | (2006.01) |
| *C08L 77/02* | (2006.01) |
| *C08L 77/06* | (2006.01) |
| *C09B 23/01* | (2006.01) |
| *C09B 23/10* | (2006.01) |
| *C09B 23/14* | (2006.01) |
| *C07D 209/12* | (2006.01) |
| *C08K 5/3417* | (2006.01) |

(52) U.S. Cl.
CPC .......... *C09B 23/105* (2013.01); *C07D 209/12* (2013.01); *C08J 3/12* (2013.01); *C08J 3/201* (2013.01); *C08K 5/3417* (2013.01); *C08L 77/02* (2013.01); *C08L 77/06* (2013.01); *C09B 23/0058* (2013.01); *C09B 23/0091* (2013.01); *C09B 23/143* (2013.01); *C08J 2333/12* (2013.01); *C08K 5/0041* (2013.01)

(58) Field of Classification Search
CPC ...... C09B 23/0058; C09B 23/02; C09B 23/01
USPC ......................................................... 548/469
See application file for complete search history.

(56) References Cited

U.S. PATENT DOCUMENTS

| | | | | |
|---|---|---|---|---|
| 2,126,852 | A * | 8/1938 | Sieglitz ................... | C09B 23/06 546/176 |
| 3,090,782 | A * | 5/1963 | Weissel ............... | C09B 23/0058 430/584 |
| 3,255,204 | A | 6/1966 | Raue et al. | |
| 3,362,953 | A * | 1/1968 | Brack .................. | C08K 5/0041 106/31.49 |
| 3,441,563 | A | 4/1969 | Weissel et al. | |
| 3,850,913 | A | 11/1974 | Psaar | |
| 4,016,172 | A | 4/1977 | Harnisch | |
| 4,628,082 | A | 12/1986 | Lorenz et al. | |
| 5,457,188 | A | 10/1995 | Zimmermann | |

FOREIGN PATENT DOCUMENTS

| | | | | | |
|---|---|---|---|---|---|
| DE | | 677207 | A | 6/1939 | |
| EP | | 599 | A1 * | 2/1979 | ............. G03G 17/04 |
| GB | | 1063320 | A * | 3/1967 | ........... C08K 5/3415 |
| GB | | 1404441 | A | 8/1975 | |
| JP | | 61210364 | A * | 9/1986 | ............. G03G 5/067 |
| JP | | 62002249 | A * | 1/1987 | ............. G03F 7/012 |
| JP | | 2014153441 | A | 8/2014 | |

OTHER PUBLICATIONS

JPO Abstract of JP-61210364-A (1986, 2 pages).*
JPO Abstract of JP-62002249-A (1987, 2 pages).*
Zitzler-Kunkel, Andre et al., "Comparative Studies on Optical, Redox, and Photovoltaic Properties of a Series of D-A-D and Analygous D-A Chromophores", Advanced Functional Materials, Wiley VCH Verlag Gmbh, 2014, pp. 4645-4653.
Gorka, Alexander P., et al., "A Near-IR Uncaging Strategy Based on Cyanine Photochemistry", JACS, 2014, American Chemical Society, pp. 14153-14159.
Zyabrev, Konstantin et al, "New 2, 2-Difluoro-1,3,2(2H) Oxazaborines and merocyanines derived from them", Dyes and Pigments, 2011, Elsevier Applied Science Publishers, 2011, pp. 749-757.
European Search Report from European Application No. 15151917, dated Apr. 7, 2015, four pages.
Schwetlick, B. K. Organikum, VEB Deutscher Verlag der Wissenschaften, Berlin, 15th edition 1977, pp. 253, 260, 674.

\* cited by examiner

*Primary Examiner* — Brieann R Johnston

(57) ABSTRACT

The present invention relates to novel methine dyes, methods for the preparation thereof and use thereof for dyeing plastics, especially polyamides, so as to obtain yellow colorings with improved light fastness and improved thermostability.

15 Claims, No Drawings

YELLOW METHINE DYES

The present invention relates to novel methine dyes, methods for the preparation thereof and use thereof for dyeing plastics.

Although there are already numerous yellow dyes on the market for coloring plastics, demand still exists for novel dyes with improved properties. In particular, there is still a need for improvement of the known dyes with respect to the two properties of color strength and thermostability. This applies in particular in the case of the application of dyes to the bulk coloration of polyamide.

The bulk coloration of synthetic polyamides presents higher requirements of the colorants used than the bulk coloration of other plastics. The melting points of synthetic polyamides are considerably higher and also the chemical reactivity of molten polyamides, especially of nylon-6.6, is substantially higher such that the heat stability of the colorants used has to be exceptionally good. There are few pigments which satisfy these high requirements, particularly if high light resistance is also additionally required.

DE-A 3543512 A1 (Bayplast yellow G) describes azo lakes which may be used for coloring polyamide in shades of yellow. Likewise known is the use of Pigment Yellow 192. EP-A 0074515 discloses nickel azobarbituric acid complexes which may likewise be used to achieve yellow coloring of polyamide.

The properties of these yellow colorants known from the prior art are not however sufficient for current technical requirements and are in particular in need of improvement regarding their fastness properties such as light and heat resistance.

The present invention relates to novel methine dyes of the formula (I)

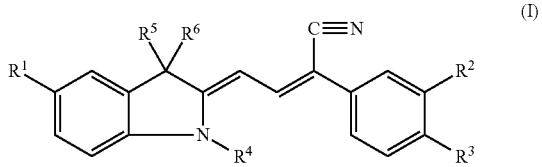

(I)

where
$R^1$ is hydrogen, halogen, COOH or COOR$^7$,
$R^2$ is hydrogen, halogen, CF$_3$, or CN,
$R^3$ is hydrogen, halogen, COOR$^8$ or CN,
$R^4$ is alkyl or phenyl
and
$R^5$ and $R^6$ are each independently alkyl,
$R^7$ is alkyl
and
$R^8$ is alkyl.

Preference is given to dyes of the formula (I), where
$R^1$ is hydrogen, halogen, COOH or COOR$^7$,
$R^2$ is hydrogen, halogen, CF$_3$, or CN,
$R^3$ is hydrogen, halogen, COOR$^8$ or CN,
$R^4$ is straight-chain or branched $C_1$-$C_4$-alkyl or phenyl
and
$R^5$ and $R^6$ are each independently straight-chain or branched $C_1$-$C_4$-alkyl,
$R^7$ is straight-chain or branched $C_1$-$C_4$-alkyl
and
$R^8$ is straight-chain or branched $C_1$-$C_4$-alkyl.

Particular preference is given to dyes of the formula (I), where
$R^1$ is hydrogen, fluorine, chlorine, COOH or COOCH$_3$,
$R^2$ is hydrogen, fluorine, chlorine, CF$_3$, or CN,
$R^3$ is hydrogen, chlorine, COOCH$_3$ or CN,
$R^4$ is methyl or phenyl,
and
$R^5$ and $R^6$ are methyl.

Using the dyes of the formula (I) according to the invention, yellow coloration of plastics, especially of polyamides, can be achieved, which are characterized, surprisingly, by improved light fastness and improved thermostability compared with the known yellow dyes used for these purposes.

It is possible using the dyes according to the invention to significantly outperform the property profiles achieved to date of known yellow dyes for plastic coloration.

The present invention further relates to the use of the dyes of the formula (I) according to the invention for the bulk coloration of plastics. The dyes according to the invention can be used here individually or in any desired mixture with one another.

Bulk coloration in this case is understood to mean in particular methods in which the dye is incorporated into the molten plastic material, e.g. with the aid of an extruder, or in which the dye is already added to the starting components for preparing the plastic, e.g. to monomers prior to polymerization.

Particularly preferred plastics are thermoplastics, for example vinyl polymers, polyesters, polyamides and also polyolefins, especially polyethylene and polypropylene, polycarbonates and polyamide. Very particular preference is given to polyamides, especially nylon-6.6, and nylon-6.

In the context of the present invention, the term polyamides is used as a designation for synthetic, industrially usable thermoplastic plastics and thus differentiates this substance class from the chemically related proteins. Almost all significant polyamides are derived from primary amines, since the repeating unit consists of the —CO—NH— functional group. In addition, polyamides of secondary amines (—CO—NR—, R=organic radical) also exist. To prepare the polyamides, in particular aminocarboxylic acids, lactams and/or diamines and dicarboxylic acids serve as monomers.

Nylon-6.6 is usually prepared from hexamethylenediamine (HMD) and adipic acid. It is formed by a polycondensation with elimination of water.

Nylon-6 is obtainable by ring-opening polymerization of ε-caprolactam with water as starter.

Suitable vinyl polymers are polystyrene, styrene-acrylonitrile copolymers, styrene-butadiene copolymers, styrene-butadiene-acrylonitrile terpolymers, polymethacrylate and polyvinyl chloride among others.

Suitable polyesters are, for example, polyethylene terephthalates, polycarbonates and cellulose esters.

The plastics to be colored may be present individually or as mixtures with one another, as plastic materials or melts.

When used for the bulk coloration of plastics, the dyes (I) according to the invention are preferably applied in finely divided form for application, wherein dispersants may be, but do not have to be, used concomitantly.

When used for the bulk coloration of plastics, the dyes (I) according to the invention can be used for example directly in the process of the plastic preparation after the polymerization is complete. In this case, at least one dye (I) according to the invention is preferably mixed in dry form or ground with the plastic granules and this mixture is plasticized and homogenized for example on mixing rollers or in screws. However, the dyes (I) according to the invention may also be added to the molten liquid material and homogeneously distributed by stirring. The material pre-colored in this way may then be further processed as usual, e.g. by spinning to give bristles, threads etc. or by extrusion or in injection molding processes to give moldings.

Since the dyes (I) are resistant to polymerization catalysts, particularly peroxides, it is also possible to add the dyes (I) according to the invention to the monomeric starting materials for the plastic preparation, e.g. of polymethyl methacrylate (PMMA) and then to polymerize in the presence of polymerization catalysts. To this end, the dye is preferably dissolved in or intimately mixed with the monomeric components.

The dyes of the formula (I) according to the invention for coloring the plastics mentioned, especially polyamide, are used preferably in amounts from 0.0001 to 1% by weight, especially 0.01 to 0.5% by weight, based on the amount of polymer.

By adding pigments insoluble in the polymers, for example titanium dioxide, it is possible to obtain corresponding useful covered colorations.

Titanium dioxide may be used in an amount from 0.01 to 10% by weight, preferably 0.1 to 5% by weight, based on the amount of polymer.

The present invention further relates to a method for the bulk coloration of plastics, wherein at least one dye of the formula (I) is mixed in dry form or is ground with at least one plastic, preferably in the form of granules, and this mixture is plasticized and homogenized, e.g. on mixing rollers or in screws.

However, the dyes (I) according to the invention may also be added to the molten liquid material and homogeneously distributed by stirring. It is likewise possible to add the dyes (I) according to the invention to the monomeric starting components in the plastic preparation and then to polymerize.

The material pre-colored in this way may then be further processed as usual, e.g. by spinning to give bristles, threads etc. or by extrusion or in injection molding processes to give moldings.

By means of the method according to the invention, transparent or covered brilliant yellow colorations with very good heat and light resistance are obtained.

To carry out the method according to the invention, it is also possible to use mixtures of the dyes of the formula (I) according to the invention with other dyes and/or inorganic and/or organic pigments.

The present invention further relates to a method for preparing the dyes of the formula (I) according to the invention.

The dyes of the formula (I) according to the invention may be prepared in a manner known per se, by reacting at least one aldehyde of the formula (II)

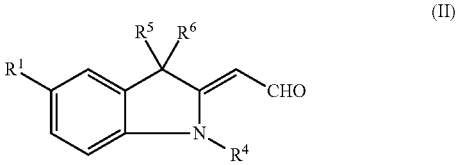

(II)

where
$R^1$, $R^4$, $R^5$ and $R^6$ have the general and preferred definitions specified for formula (I), with at least one phenylacetonitrile derivative of the formula (III)

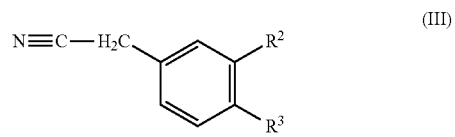

(III)

where
$R^2$ and $R^3$ have the general and preferred definitions specified for formula (I).

The method for preparing the dyes (I) according to the invention by reacting the aldehydes of the formula (II) with the phenylacetonitrile derivatives of the formula (III) may be carried out in a manner known per se.

The method for preparing the dyes (I) according to the invention is carried out generally at a temperature in the range from −10 to 180° C., preferably from 0 to 100° C. and particularly preferably from 10 to 90° C.

The method for preparing the dyes (I) according to the invention is carried out generally at a pressure from 0.9 to 1.1 bar, preferably at standard pressure.

The method for preparing the dyes (I) according to the invention can be carried out in the presence of at least one solvent. Suitable solvents are those from the series of alcohols and formamides for example. The method for preparing the dyes (I) according to the invention is preferably carried out in the presence of at least one alcohol from the series of methanol, ethanol, propanol, and/or at least one formamide from the series of dimethylformamide and diethylformamide, particularly preferably in the presence of methanol and/or dimethylformamide.

The method for preparing the dyes (I) according to the invention can be carried out in the presence of at least one base. Suitable bases are, for example, alkali metal hydroxides and alkali metal alkoxides. Preference is given to using lithium hydroxide, sodium hydroxide, potassium hydroxide and/or potassium tert-butoxide, particularly preferably sodium hydroxide and/or potassium tert-butoxide.

In general, the method for preparing the dyes (I) according to the invention is carried out such that the aldehyde (II) is firstly initially charged and the phenylacetonitrile derivative (III) is added and, after reaction is complete, the compounds of the formula (I) is isolated. The isolation can be carried out by customary processes, preferably by filtration. The reaction product obtained can optionally be worked-up by further method steps such as washing and drying.

To carry out the method, generally 0.8 to 1.5 mol of phenylacetonitrile derivative (III) is used per mole of aldehyde (II). Preferably, 0.9 to 1.1 mol of phenylacetonitrile derivative (III) is used per mole of aldehyde (II) and particularly preferably 1 mol of phenylacetonitrile derivative (III) is used per mole of aldehyde (II).

Phenylacetonitrile derivatives of the formula (III) are known and can be purchased as commercial products from Alfa Acer for example.

The aldehydes of the formula (II) are novel and also form part of the subject matter of the present invention.

They may be prepared, for example, in a two-stage synthesis in a manner known to those skilled in the art. Here, in a first stage a), at least one indole derivative of the formula (IV)

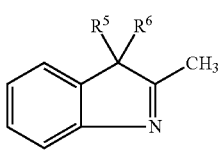

(IV)

where
R⁵ and R⁶ have the general and preferred definitions specified for formula (I),
is reacted with at least one alkylating reagent and subsequently, in a second stage b), the intermediate of the first stage is reacted with at least one formylation reagent.

Reactions of the kind described in stage b) are known in the literature under the name of Vilsmeier reaction.

Generally, the reaction in stage a) is carried out such that the indole derivative of the general formula (IV) is initially charged and the alkylating agent is added optionally in the presence of a solvent.

The first stage a) of the reaction is carried out generally at a temperature in the range from 10 to 80° C., preferably from 20 to 70° C. and particularly preferably from 30 to 60° C.

The reaction in stage a) is carried out generally at a pressure from 0.9 to 1.1 bar, preferably at standard pressure.

The reaction in stage a) may be carried out in the presence of at least one solvent. Suitable solvents are those from the series of alcohols and water for example. The reaction in stage a) is preferably carried out in the presence of water as solvent.

In principle, all known alkylating reagents are suitable as alkylating reagent (see e.g. B. K. Schwetlick, Organikum, VEB Deutscher Verlag der Wissenschaften, Berlin, 15th edition 1977, pages 260, 253, 674), such as dimethyl sulfate, methyl iodide or diazomethane. Preference is given to the use of dimethyl sulfate.

In general, at least one mole of alkylating reagent is used per mole of indole derivative. Depending on the structure of the indole derivative, corresponding to the above stoichiometry, even higher molar amounts may be used. Preferably, 0.9 to 1.1 mol, particularly preferably 1 mol of alkylating reagent is used per mole of indole derivative (IV).

The intermediate prepared in stage a) can be isolated by customary methods, by filtration for example. The intermediate prepared in stage a) is preferably further reacted directly without isolation in the subsequent stage b).

In general, the reaction in stage b) is carried out in such a manner that the alkylated compound from the first stage a) in the form of the reaction solution obtained is initially charged and the formylation reagent is added, optionally in the presence of at least one solvent, and subsequently the aldehyde of the formula (II) thus prepared is precipitated, optionally by the addition of a suitable amount of a suitable precipitant, and the aldehyde of the formula (II) is then isolated by customary methods, by filtration for example.

The reaction in stage b) is carried out generally at a temperature in the range from 10 to 80° C., preferably from 20 to 70° C. and particularly preferably from 30 to 60° C.

The reaction in stage b) is carried out generally at a pressure from 0.9 to 1.1 bar, preferably at standard pressure.

The reaction in stage b) may be carried out in the presence of at least one solvent. Suitable solvents are formamides for example. Preference is given to dimethylformamide and diethylformamide, particular preference being given to the use of dimethylformamide. When using dimethylformamide, it is particularly preferable to use this in excess wherein the dimethylformamide then serves as formylation reagent and solvent at the same time.

The formylation reagent used in stage b) is generally a mixture of at least one formamide and at least one phosphoric acid chloride.

Preferred formamides are dimethylformamide, diethylformamide and dibutylformamide. A preferred phosphoric acid chloride is phosphorus oxychloride.

The formylation reagent used is particularly preferably a mixture of dimethylformamide and phosphorus oxychloride.

In general, at least one mole of formylation reagent, preferably 1.1 to 1.5 mol and particularly preferably 1.1 to 1 mol, is used per mole of alkylated compound from stage 1.

Suitable precipitants are, for example, alcohols such as methanol and/or ethanol.

The precipitant used is preferably methanol and/or ethanol, especially methanol.

The indole derivatives of the formula (IV) are known to those skilled in the art. They may be prepared in a manner known per se in a two-stage synthesis by reacting an aniline derivative of the formula (V)

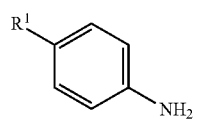

(V)

where
R¹ has the general and preferred definition specified for formula (I),
with a diazotization reagent and subsequent reaction with ring closure with a ketone of the formula (VI)

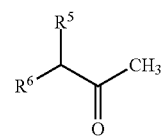

(VI)

where
R⁵ and R⁶ have the general and preferred definition specified for formula (I).

The diazotization reaction is generally carried out by initially charging the aniline derivative and adding the diazotization reagent at a temperature in the range from 0 to 10° C. at standard pressure in an aqueous medium.

In principle, any suitable diazotization reagent is an option as diazotization reagent. Preference is given to using an aqueous sodium nitrite solution.

In general, the diazotization reagent is used in an amount of at least two moles based on the aniline derivative (V).

The ring closure reaction with the ketone of the formula (VI) is carried out in a manner known per se in a one-pot reaction by reducing the diazonium salt of the aniline derivative (V) to the hydrazone and by reacting the hydrazone with the ketone of the general formula (VI), preferably at a temperature in the range from 40 to 100° C., preferably in aqueous solution, and subsequently by isolating and washing the indole derivative of the formula (IV) by customary methods, preferably filtration.

The aniline derivatives of the formula (V) and the ketones of the formula (VI) are known and can be purchased as commercial products, from Alfa Acer or Sigma-Aldrich for example.

The invention is elucidated but not limited by the following examples, in which the parts are by weight and percentage values are percent by weight (% by weight).

1) Preparation of the Inventive Compounds of the Formula (I)

Example 1

Preparation of the Compound According to the Invention where $R^1$=—$COOCH_3$, $R^2$ and $R^3$=Cl, $R^4$=—$CH_3$ and $R^5$ and $R^6$=—$CH_3$ In a charge of 100 ml of methanol, 25.9 g (=0.1 mol) of aldehyde of the formula (II), where $R^1$=—$COOCH_3$, $R^4$=—$CH_3$ and $R^5$ and $R^6$=—$CH_3$, and 18.6 g (=0.1 mol) of 3,4-dichlorophenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water at a temperature of 90° C. The washed product was dried in a vacuum drying cabinet at a temperature of 80° C. and a pressure of 200 mbar.

Yield: 32.5 g (corresponds to 76% of theory), melting point 241° C.

Example 2

Preparation of the Compound According to the Invention where $R^1$=—$COOCH_3$, $R^2$=H, $R^3$=Cl, $R^4$=—$CH_3$ and $R^5$ and $R^6$=—$CH_3$ In a charge of 100 ml of methanol, 25.9 g (=0.1 mol) of aldehyde of the formula (II), where $R^1$=—$COOCH_3$, $R^4$=—$CH_3$ and $R^5$ and $R^6$=—$CH_3$, and 15.2 g (=0.1 mol) of 4-chlorophenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 31.0 g (corresponds to 79% of theory), melting point 199° C.

Example 3

Preparation of the Compound According to the Invention where $R^1$=—$COOCH_3$, $R^2$=Cl, $R^3$=H, $R^4$=—$CH_3$ and $R^5$ and $R^6$=—$CH_3$ In a charge of 100 ml of methanol, 25.9 g (=0.1 mol) of aldehyde of the formula (II), where $R^1$=—$COOCH_3$, $R^4$=—$CH_3$ and $R^5$ and $R^6$=—$CH_3$, and 15.2 g (=0.1 mol) of 3-chlorophenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 29.5 g (corresponds to 75% of theory), melting point 130° C.

Example 4

Preparation of the Compound According to the Invention where $R^1$=—$COOCH_3$, $R^2$=H, $R^3$=—$COOCH_3$, $R^4$=—$CH_3$ and $R^5$ and $R^6$=—$CH_3$ In a charge of 200 ml of methanol, 25.9 g (=0.1 mol) of aldehyde of the formula (II), where $R^1$=—$COOCH_3$, $R^4$=—$CH_3$ and $R^5$ and $R^6$=—$CH_3$, and 17.5 g (=0.1 mol) of methyl 4-(cyanomethyl)benzoate were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 31.2 g (corresponds to 75% of theory), melting point 246° C.

Example 5

Preparation of the Compound According to the Invention

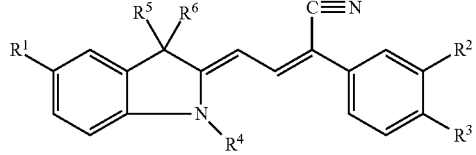

where $R^1$=—COOCH$_3$, $R^2$=H, $R^3$=CN, $R^4$=—CH$_3$ and $R^5$ and $R^6$=—CH$_3$ In a charge of 200 ml of methanol, 25.9 g (=0.1 mol) of aldehyde of the formula (II), where $R^1$=—COOCH$_3$, $R^4$=—CH$_3$ and $R^5$ and $R^6$=—CH$_3$, and 14.2 g (=0.1 mol) of 4-cyanophenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 26.8 g (corresponds to 70% of theory), melting point 269° C.

Example 6

Preparation of the Compound According to the Invention

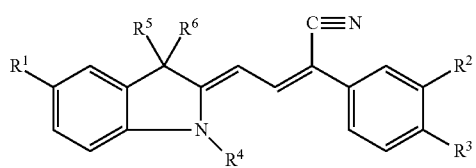

where $R^1$=—COOCH$_3$, $R^2$=F, $R^3$=H, $R^4$=—CH$_3$ and $R^6$=—CH$_3$

In a charge of 200 ml of methanol, 25.9 g (=0.1 mol) of aldehyde of the formula (II), where $R^1$=—COOCH$_3$, $R^4$=—CH$_3$ and $R^5$ and $R^6$=—CH$_3$, and 13.5 g (=0.1 mol) of 3-fluorophenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 24.5 g (corresponds to 65% of theory), melting point 311° C.

Example 7

Preparation of the Compound According to the Invention

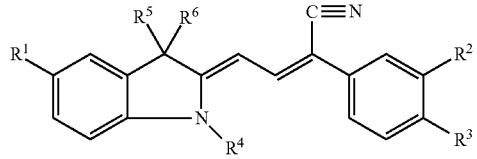

where $R^1$=—COOCH$_3$, $R^2$=CF$_3$, $R^3$=H, $R^4$=—CH$_3$ and $R^5$ and $R^6$=—CH$_3$ In a charge of 200 ml of methanol, 25.9 g (=0.1 mol) of aldehyde of the formula (II), where $R^1$=—COOCH$_3$, $R^4$=—CH$_3$ and $R^5$ and $R^6$=—CH$_3$, and 13.5 g (=0.1 mol) of 3-(trifluoromethyl)phenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 24.5 g (corresponds to 65% of theory), melting point 199° C.

Example 8

Preparation of the Compound According to the Invention

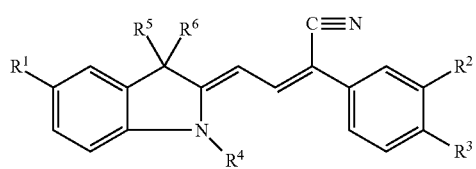

where $R^1$=—Cl, $R^2$ and $R^3$=C, $R^4$=—CH$_3$ and $R^5$ and $R^6$=—CH$_3$

In a charge of 200 ml of methanol, 11.8 g (=0.05 mol) of aldehyde of the formula (II), where $R^1$=—Cl, $R^4$=—CH$_3$ and $R^5$ and $R^6$=—CH$_3$, and 9.3 g (=0.05 mol) of 3,4-dichlorophenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 18.2 g (corresponds to 90% of theory), melting point 239° C.

Example 9

Preparation of the Compound According to the Invention

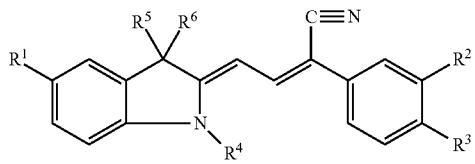

where $R^1$=—F, $R^2$ and $R^3$=Cl, $R^4$=—$CH_3$ and $R^5$ and $R^6$=—$CH_3$

In a charge of 200 ml of methanol, 11.0 g (=0.05 mol) of aldehyde of the formula (II), where $R^1$=—F, $R^4$=—$CH_3$ and $R^5$ and $R^6$=—$CH_3$, and 9.3 g (=0.05 mol) of 3,4-dichlorophenylacetonitrile were introduced. Subsequently, the pH was adjusted to around 10 with ca. 1 g of a 50% aqueous potassium hydroxide solution and the reactor contents were heated to a temperature of 60° C. and then stirred for ca. 6 hours. The mixture was then cooled to 25° C. and the reaction product isolated on a Nutsche filter. The filter cake was washed with ca. 50 ml of methanol and ca. 500 ml of water (T=90° C.). The washed product was dried in a vacuum drying cabinet at a temperature of 80° C. and a pressure of 200 mbar.

Yield: 13.6 g (corresponds to 70% of theory), melting point 238° C.

2) Preparation of the Precursors

Example 10

Preparation of an Aldehyde of the Formula (II)

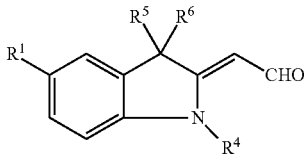

where $R^1$=—$COOCH_3$, $R^4$=—$CH_3$ and $R^5$ and $R^6$=—$CH_3$ a) Preparation of the Diazotization:

In a charge of 270 g of 30% hydrochloric acid, 139.9 g of p-aminobenzoic acid were introduced and the mixture was cooled to 0° C. by externally cooling. Subsequently, ca. 174 g of a 40% aqueous solution of sodium nitrite were added. After stirring for ca. 30 minutes, the nitrite excess was removed with ca. 0.5 g of amidosulfonic acid.

b) Preparation of the Hydrazone and Ring Closure:

In a charge of 250 g of water and 660 g of 39% sodium hydrogen sulfite, the pH was adjusted to ca. 6.5 with ca. 80 g of a 40% aqueous sodium hydroxide solution. Over the course of ca. 30 min, the diazotization solution described above was transferred while maintaining a pH of ca. 6.5 with ca. 100 g of a 40% aqueous sodium hydroxide solution.

The mixture was then stirred at a temperature of 40° C. for ca. 1 hour. Subsequently, 560 g of sulfuric acid (96%) and then 86.1 g of methyl isopropyl ketone were added dropwise. The reactor contents were heated to 70° C. and then stirred for ca. 4 hours. The reactor contents were subsequently heated to 80° C. and then stirred for ca. 4 hours. The reactor contents were then cooled to 25° C. and the pH was adjusted to ca. 6.5 with ca. 800 g of a 40% aqueous sodium hydroxide solution. After stirring for 30 minutes, the reaction product was isolated on a Nutsche filter and washed with 2 liters of water.

c) Preparation of the Aldehyde:

In a charge of 1200 g of water, the water-moist press cake of the ring closure product from stage b) was introduced. The pH was then adjusted to ca. 10 with ca. 70 g of a 40% aqueous sodium hydroxide solution. Over the course of ca. 1 hour, 325 g of dimethyl sulfate were added dropwise maintaining a pH here of ca. 8.5 by addition of ca. 200 g of a 40% aqueous sodium hydroxide solution. The reactor contents were heated to 40° C. and then stirred for ca. 5 hours. The reactor contents were subsequently heated to 60° C. and then stirred for ca. 1 hour. The reaction mixture was allowed to stand for ca. 1 hour until phase separation had occurred. The aqueous phase was then removed. Residual water was removed from the organic phase under reduced pressure at 80° C. and 20 mbar. 310 g of dimethylformamide were then added dropwise to the organic phase. Subsequently, 263 g of phosphorus oxychloride were metered in at 40° C. over the course of 3 hours. The reactor contents were then stirred for 5 hours. The mixture was then cooled to 20° C. and 160 g of methanol were added. The pH was then adjusted to ca. 11 with ca. 200 g of a 40% aqueous sodium hydroxide solution. After stirring for 60 minutes, the reaction product was isolated on a Nutsche filter and washed with 160 g of methanol and 2000 g of water. The washed product was dried in a vacuum drying cabinet at a temperature of 80° C. and a pressure of 200 mbar.

Yield: 176.3 g (corresponds to 68% of theory)

Example 11

Preparation of an Aldehyde of the Formula (II)

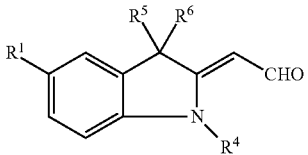

where $R^1$=Cl, $R^4$=$CH_3$ and $R^5$ and $R^6$=$CH_3$ a) Preparation of the Diazotization:

In a charge of 268 g of 30% hydrochloric acid, 127.6 g of 4-chloroaniline were added dropwise and the mixture was cooled to 0° C. by externally cooling. Subsequently, ca. 174 g of a 40% aqueous solution of sodium nitrite were added. After stirring for ca. 30 minutes, the nitrite excess was removed with ca. 0.5 g of amidosulfonic acid.

b) Preparation of the Hydrazone and Ring Closure:

In a charge of 250 g of water and 660 g of 39% sodium hydrogen sulfite, the pH was adjusted to ca. 6.5 with ca. 80 g of a 40% aqueous sodium hydroxide solution. Over the course of ca. 30 minutes, the diazotization solution from stage a) described above was transferred while maintaining a pH of ca. 6.5 by addition of ca. 100 g of a 40% aqueous sodium hydroxide solution. The mixture was then stirred at a temperature of 40° C. for ca. 1 hour. Subsequently, 560 g of sulfuric acid (96%) and then 86.1 g of methyl isopropyl ketone were added dropwise. The reactor contents were heated to 70° C. and then stirred for ca. 4 hours. The reactor contents were subsequently heated to 80° C. and then stirred for ca. 4 hours. The reactor contents were then cooled to 25°

C. and the pH was adjusted to ca. 6.5 with ca. 800 g of a 40% aqueous sodium hydroxide solution. After stirring for 30 minutes, the reaction product is isolated on a Nutsche filter and washed with 2 liters of water.

c) Preparation of the Aldehyde:

In a charge of 1200 g of water, the water-moist press cake of the ring closure product from stage b) was introduced. The pH was then adjusted to ca. 10 with ca. 5 g of a 40% aqueous sodium hydroxide solution. Over the course of ca. 1 hour, 153 g of dimethyl sulfate were added dropwise maintaining a pH here of ca. 8.5 by addition of ca. 90 g of a 40% aqueous sodium hydroxide solution. The reactor contents were heated to 40° C. and then stirred for ca. 5 hours. The reactor contents are subsequently heated to 60° C. and then stirred for ca. 1 hour.

The reaction mixture was allowed to stand for ca. 1 hour until phase separation had occurred. The aqueous phase was then removed. Residual water was removed from the organic phase under reduced pressure at 80° C. and 20 mbar. 275 g of dimethylformamide were then added dropwise to the organic phase.

Subsequently, 116 g of phosphorus oxychloride were metered in at 40° C. over the course of 3 hours. The reactor contents were then stirred for 5 hours, then cooled to 20° C. and 160 g of methanol were added. The pH was then adjusted to ca. 11 with ca. 180 g of a 40% aqueous sodium hydroxide solution. After stirring for 60 minutes, the reaction product was isolated on a Nutsche filter and washed with 160 g of methanol and 2000 g of water. The washed product was dried in a vacuum drying cabinet at a temperature of 80° C. and a pressure of 200 mbar.

Yield: 141.4 g (corresponds to 60% of theory)

Example 12

Preparation of an Aldehyde of the Formula (II)

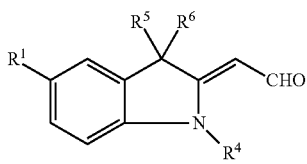

where $R^1$=F, $R^4$=—$CH_3$ and $R^5$ and $R^6$=—$CH_3$ a) Preparation of the Diazotization:

In a charge of 375 g of 30% hydrochloric acid, 155.5 g of 4-fluoroaniline were added dropwise and the mixture was cooled to 0° C. by externally cooling. Subsequently, ca. 244 g of a 40% aqueous solution of sodium nitrite were added. After stirring for ca. 30 minutes, the nitrite excess was removed with ca. 0.5 g of amidosulfonic acid.

b) Preparation of the Hydrazone and Ring Closure:

In a charge of 250 g of water and 918 g of sodium hydrogen sulfite solution (39%), the pH was adjusted to ca. 6.5 by the addition of ca. 120 g of a 40% aqueous sodium hydroxide solution. Over the course of ca. 30 minutes, the diazotization solution from stage a) described above was transferred while maintaining a pH of ca. 6.5 by addition of ca. 140 g of a 40% aqueous sodium hydroxide solution. The mixture was then stirred at a temperature of 40° C. for ca. 1 hour. Subsequently, 776 g of 96% sulfuric acid and then 120.4 g of methyl isopropyl ketone were added dropwise. The reactor contents were heated to 70° C. and then stirred for ca. 4 hours. The reactor contents were subsequently heated to 80° C. and then stirred for ca. 4 hours. The reactor contents were then cooled to 25° C. and the pH was adjusted to ca. 6.5 with ca. 1150 g of a 40% aqueous sodium hydroxide solution. After stirring for 30 minutes, the reaction product was isolated on a Nutsche filter and washed with 2 liters of water.

c) Preparation of the Aldehyde:

In a charge of 1200 g of water, the water-moist press cake of the ring closure product from stage b) was introduced. The pH was then adjusted to ca. 10 with ca. 10 g of a 40% aqueous sodium hydroxide solution. Over the course of ca. 1 hour, 194 g of dimethyl sulfate were added dropwise maintaining a pH here of ca. 8.5 by addition of ca. 120 g of a 40% aqueous sodium hydroxide solution. The reactor contents were heated to 40° C. and then stirred for ca. 5 hours. The reactor contents were subsequently heated to 60° C. and then stirred for ca. 1 hour. The reaction mixture was allowed to stand for ca. 1 hour until phase separation had occurred. The aqueous phase was then removed. Residual water was removed from the organic phase under reduced pressure at 80° C. and 20 mbar. 350 g of dimethylformamide were then added dropwise to the organic phase. Subsequently, 147 g of phosphorus oxychloride were metered in at 40° C. over the course of 3 hours. The reactor contents were then stirred for 5 hours, then cooled to 20° C. and 160 g of methanol were added. The pH was then adjusted to ca. 11 by addition of ca. 200 g of a 40% aqueous sodium hydroxide solution. After stirring for 60 minutes, the reaction product was isolated on a Nutsche filter and washed with 160 g of methanol and 2000 g of water. The washed product was dried in a vacuum drying cabinet at a temperature of 80° C. and a pressure of 200 mbar.

Yield: 162.8 g (corresponds to 53% of theory)

List of Substances Purchased:

| Name: | Molecular weight | Cas. No. | Content: | Manufacturer: |
|---|---|---|---|---|
| p-Aminobenzoic acid | 137.2 | 150-13-0 | 98 | Sigma-Aldrich |
| Methyl isopropyl ketone | 86.1 | 563-80-4 | 99 | Sigma-Aldrich |
| Isopropyl methyl ketone | | | | |
| 4-Chloroaniline | 127.6 | 106-47-8 | 98 | Sigma-Aldrich |
| 4-Fluoroaniline | 111.1 | 371-40-4 | 99 | Alfa Acer |
| 3, 4-Dichlorophenylacetonitrile | 186.0 | 3218-49-3 | 98 | Alfa Acer |
| 4-Chlorophenylacetonitrile | 151.6 | 140-53-4 | 98 | Alfa Acer |
| 3-Chlorophenylacetonitrile | 151.6 | 1529-41-5 | 99 | Alfa Acer |
| Methyl 4-(cyanomethyl)benzoate | 175.2 | 76469-88-0 | 96 | Sigma-Aldrich |
| 4-Cyanophenylacetonitrile | 142.2 | 876-31-3 | 97 | Alfa Acer |
| 3-Fluorophenylacetonitrile | 135.1 | 501-00-8 | 98 | Alfa Acer |
| 3-(Trifluoromethyl)phenylacetonitrile | 185.2 | 10036-43-8 2338-76-3 | 97 | Sigma-Aldrich |

The results of the UV/VIS measurements and absorption values for the inventive compounds of Examples 1 to 9 are listed in Table 1.

TABLE 1

| Compound of | Absorption maximum UV/VIS spectrum[1] | E 1/1 value[2] |
|---|---|---|
| Example 1 | 427 nm | 2498 |
| Example 2 | 419 nm | 1926 |
| Example 3 | 425 nm | 1402 |
| Example 4 | 440 nm | 1326 |
| Example 5 | 445 nm | 1464 |
| Example 6 | 419 nm | 1141 |
| Example 7 | 422 nm | 1128 |
| Example 8 | 430 nm | 1230 |
| Example 9 | 428 nm | 1156 |

[1] The UV/VIS absorption spectra of the inventive compounds were all measured in the solvent 1-methoxy-2-propyl acetate (CAS No. 108-65-6).
[2] The E1/1 value specified is a hypothetical absorption value which would be obtained if a 1 percent solution by weight of the respective compound (dissolved in 1-methoxy-2-propyl acetate) were to be measured in a cuvette with a 1 cm path length.

3) Practical Results

A) Description of the "Thermostability" Test Method

In a tumbling mixer, 2 g each of the dye to be tested were mixed with 1998 g of a PA6 granulate of the Durethan B30S type (commercial product from Lanxess Deutschland GmbH) with 1% TiO2 which had been dried at 80° C. for 4 hours. This mixture was extruded at a material temperature of at most 240° C. in a single-screw extruder (Stork, 25 mm screw), cooled with water, granulated using a granulator from Sheer and dried at 80° C. for 8 hours. The heat stability of the resulting plastic granules was tested according to DIN EN 12877-2 ("Determination of colour stability to heat during processing of colouring materials in plastics") (method A) on an injection molding machine. A sample as standard was prepared at 240° C. with a residence time in the screw of 2.5 minutes. Compared to this standard sample, the samples to be determined were evaluated coloristically, which were prepared at a residence time of 5 minutes and temperatures of 240-320° C. Samples with an overall color difference of dE≤3.0 were evaluated as stable at the applied temperature.

The results of the thermostability determination of the inventive compounds of Examples 1 to 9 and also the non-inventive compounds of the prior art are listed in Table 2.

TABLE 2

| Inventive compound | Heat stable to (° C.) |
|---|---|
| Example 1 | 300 |
| Example 2 | 320 |
| Example 3 | 320 |
| Example 4 | 280 |
| Example 5 | 260 |
| Example 6 | 300 |
| Example 7 | 280 |
| Example 8 | 320 |
| Example 9 | 320 |

Non-Inventive Comparative Compounds

| | |
|---|---|
| D.Y 201 (Macrolex Yellow 6G) | Decolorization at 240° C. |
| S.Y. 93 (Macrolex Yellow 3G) | Decolorization at 240° C. |
| S.Y 114 (Macrolex Yellow G) | 240° C. |
| S.Y 160:1 (Macrolex Fluor. Yellow 10GN) | <240° C. (dE 3.6 at 240° C.) |

What is claimed is:

1. A methine dye of the formula (I)

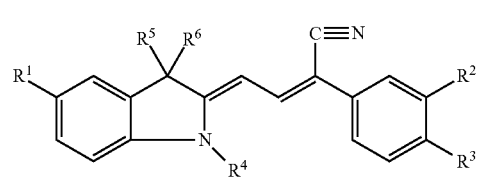

where
$R^1$ is hydrogen, halogen, COOH or $COOR^7$,
$R^2$ is hydrogen, halogen, $CF_3$, or CN,
$R^3$ is hydrogen, halogen, $COOR^8$ or CN,
$R^4$ is alkyl or phenyl,
$R^5$ and $R^6$ are each independently alkyl,
$R^7$ is alkyl, and
$R^8$ is alkyl.

2. The methine dye as claimed in claim 1, wherein:
$R^4$ is straight-chain or branched $C_1$-$C_4$-alkyl or phenyl,
$R^5$ and $R^6$ are each independently straight-chain or branched $C_1$-$C_4$-alkyl,
$R^7$ is straight-chain or branched $C_1$-$C_4$-alkyl, and
$R^8$ is straight-chain or branched $C_1$-$C_4$-alkyl.

3. The methine dye as claimed in claim 1, wherein:
$R^1$ is hydrogen, fluorine, chlorine, COOH or $COOCH_3$,
$R^2$ is hydrogen, fluorine, chlorine, $CF_3$, or CN,
$R^3$ is hydrogen, chlorine, $COOCH_3$ or CN,
$R^4$ is methyl or phenyl, and
$R^5$ and $R^6$ are methyl.

4. The methine dye as claimed in claim 1, wherein for formula (I):
$R^1$ is —$COOCH_3$, $R^2$ and $R^3$ are Cl, $R^4$ is —$CH_3$, and $R^5$ and $R^6$ are —$CH_3$, or
$R^1$ is —$COOCH_3$, $R^2$ is H, $R^3$ is Cl, $R^4$ is —$CH_3$, and $R^5$ and $R^6$ are —$CH_3$, or
$R^1$ is —$COOCH_3$, $R^2$ is Cl, $R^3$ is H, $R^4$ is —$OH_3$, and $R^5$ and $R^6$ are —$CH_3$, or
$R^1$ is —$COOCH_3$, $R^2$ is H, $R^3$ is —$COOCH_3$, $R^4$ is —$CH_3$, and $R^5$ and $R^6$ are —$CH_3$, or
$R^1$ is —$COOCH_3$, $R^2$ is H, $R^3$ is CN, $R^4$ is —$CH_3$, and $R^5$ and $R^6$ are —$CH_3$, or
$R^1$ is —$COOCH_3$, $R^2$ is F, $R^3$ is H, $R^4$ is —$CH_3$, and $R^5$ and $R^6$ are —$CH_3$, or
$R^1$ is —$COOCH_3$, $R^2$ is $CF^3$, $R^3$ is H, $R^4$ is —$CH_3$, and $R^5$ and $R^6$ are —$CH_3$, or
$R^1$ is —Cl, $R^2$ and $R^3$ are Cl, $R^4$ is —$CH_3$, and $R^5$ and $R^6$ are —$CH_3$, or
$R^1$ is —F, $R^2$ and $R^3$ are Cl, $R^4$ is —$CH_3$, and $R^5$ and $R^6$ are —$CH_3$.

5. A method for the bulk coloration of plastics with at least one methine dye of the formula (I)

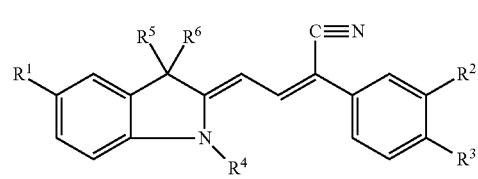

where
$R^1$ is hydrogen, halogen, COOH or $COOR^7$,
$R^2$ is hydrogen, halogen, $CF_3$, or CN, R³ is hydrogen, halogen, COOR⁸ or CN,
R⁴ is alkyl or phenyl,
R⁵ and R⁶ are each independently alkyl,
R⁷ is alkyl, and
R⁸ is alkyl,
the method comprising incorporating the at least one methine dye into at least one plastic.

6. The method as claimed in claim 5, wherein the plastic comprises a thermoplastic.

7. The method as claimed in claim 6, wherein the plastic is at least one plastic from the series of vinyl polymers, polyesters, polyolefins, polycarbonates and polyamides.

8. The method as claimed in claim 6, wherein the plastic is nylon-6 and/or nylon-6,6, and the methine dye is used in an amount of 0.01 to 0.5% by weight, based on the amount of plastic.

9. The method as claimed in claim 5, wherein the methine dye is used in an amount from 0.0001 to 1% by weight, based on the amount of plastic.

10. The method for the bulk coloration of plastics according to claim 5, wherein the incorporating comprises one of:
  melting a plastic material comprising at least one plastic, and adding the at least one methine dye to the molten plastic material to produce a mixture, and homogenizing the mixture;
  mixing the at least one methine dye in dry form with at least one comminuted plastic to produce a mixture, and melting and homogenizing the mixture; and
  grinding the at least one methine dye in dry form with at least one plastic to produce a mixture, and melting and homogenizing the mixture.

11. The method for the bulk coloration of plastics according to claim 5, wherein the incorporating comprises:
  mixing the at least one methine dye with monomeric starting components for preparing the at least one plastic; and
  subsequently polymerizing the mixture.

12. The method for the bulk coloration of plastics according to claim 11, wherein the plastic is polymethyl methacrylate (PMMA), the starting components comprise at least one methyl methacrylate monomer, and the polymerizing is done in the presence of at least one polymerization catalyst.

13. A plastic composition comprising at least one methine dye of the formula (I)

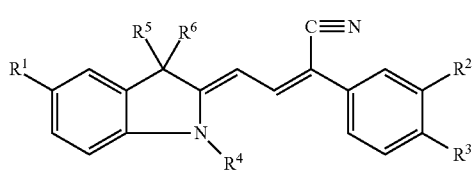

where
  R¹ is hydrogen, halogen, COOH or COOR⁷,
  R² is hydrogen, halogen, CF₃, or CN,
  R³ is hydrogen, halogen, COOR⁸ or CN,
  R⁴ is alkyl or phenyl,
  R⁵ and R⁶ are each independently alkyl,
  R⁷ is alkyl, and
  R⁸ is alkyl.

14. A molding comprising at least one plastic composition comprising a methine dye of the formula (I)

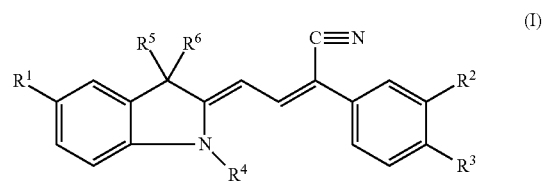

where
  R¹ is hydrogen, halogen, COOH or COOR⁷,
  R² is hydrogen, halogen, CF₃, or CN,
  R³ is hydrogen, halogen, COOR⁸ or CN,
  R⁴ is alkyl or phenyl,
  R⁵ and R⁶ are each independently alkyl,
  R⁷ is alkyl, and
  R⁸ is alkyl.

15. A method for preparing a methine dye of the formula (I)

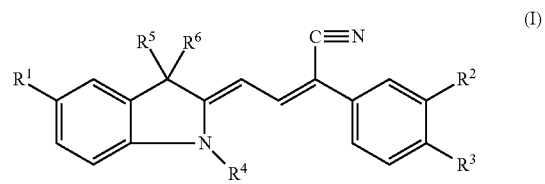

where R¹-R⁶ are as indicated below,
the method comprising contacting at least one aldehyde of the formula (II)

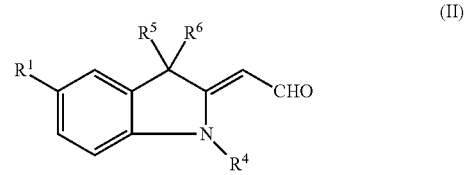

where
  R¹ is hydrogen, halogen, COOH or COOR⁷,
  R⁴ is alkyl or phenyl,
  R⁵ and R⁶ are each independently alkyl, and
  R⁷ is alkyl,
with at least one phenylacetonitrile derivative of the formula (III)

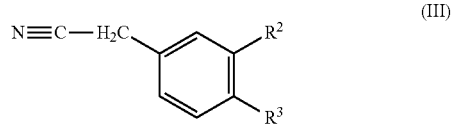

where
  R² is hydrogen, halogen, CF₃, or CN,
  R³ is hydrogen, halogen, COOR⁸ or CN, and
  R⁸ is alkyl.

* * * * *